United States Patent [19]
Miyawaki et al.

[11] Patent Number: 5,906,628
[45] Date of Patent: May 25, 1999

[54] ULTRASONIC TREATMENT INSTRUMENT

[75] Inventors: Makoto Miyawaki, Tanashi; Mitsumasa Okada, Hachioji, both of Japan

[73] Assignee: Olympus Optical Co., Ltd., Tokyo, Japan

[21] Appl. No.: 08/842,637

[22] Filed: Apr. 16, 1997

[30] Foreign Application Priority Data

Jun. 26, 1996 [JP] Japan .................................. 8-165806
Jun. 26, 1996 [JP] Japan .................................. 8-166051

[51] Int. Cl.⁶ .................................................. A61B 17/32
[52] U.S. Cl. ............................................ 606/169; 606/171
[58] Field of Search ................................. 604/22; 601/2; 606/169–171, 128

[56] References Cited

U.S. PATENT DOCUMENTS 3,636,943  1/1972  Balamuth .
5,154,694  10/1992  Kelman ..................... 604/22
5,322,055  6/1994  Davison et al. .

FOREIGN PATENT DOCUMENTS

WO 93/14709  8/1993  WIPO .

*Primary Examiner*—Ruth S. Smith
*Attorney, Agent, or Firm*—Frishauf, Holtz, Goodman, Langer & Chick

[57] ABSTRACT

An ultrasonic treatment instrument includes an ultrasonic transducer for generating ultrasonic oscillation, a hand piece containing the ultrasonic transducer, and a probe having a proximal end portion connected to the ultrasonic transducer and a distal end portion to which the ultrasonic oscillation of the ultrasonic transducer is transmitted. A sheath covers the probe and has a front end portion extending toward the distal end portion of the probe and a rear end portion connected to the hand piece. A hook-shaped treatment section is provided at the distal end portion of the probe and has a hook portion bent which is substantially perpendicular to an axis of the sheath and an axial body extending from a proximal end of the bent hook portion. The axial body is eccentric with respect to the axis of the sheath, and an operating section is provided which moves the sheath and the probe relative to each other along the axis of the sheath to thereby enable an organic tissue to be held between the hook-shaped treatment section and the front end portion of the sheath.

22 Claims, 11 Drawing Sheets

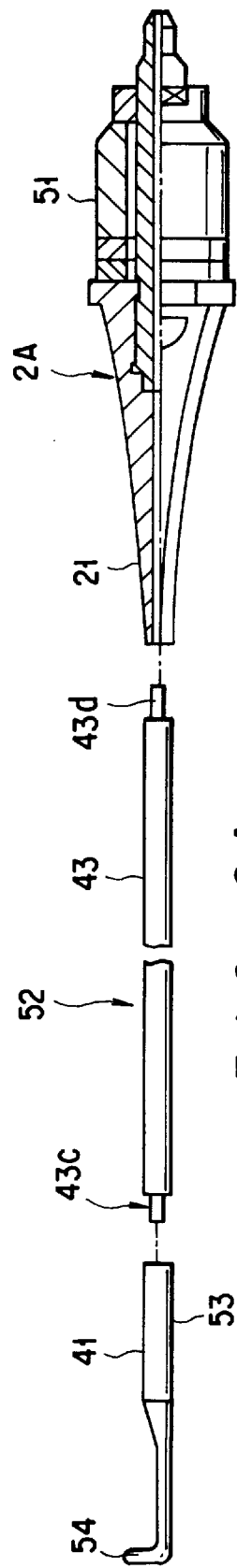
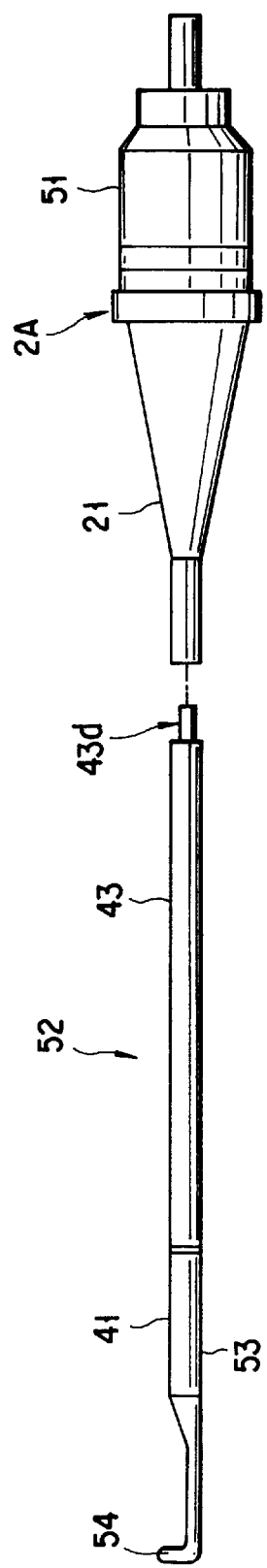
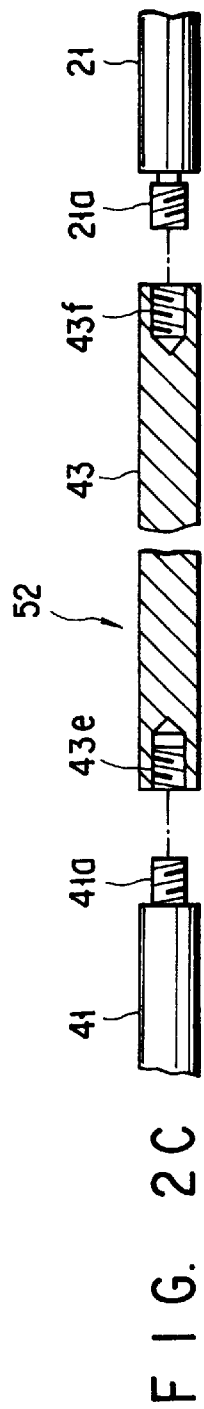
F I G. 2A F I G. 2B F I G. 2C

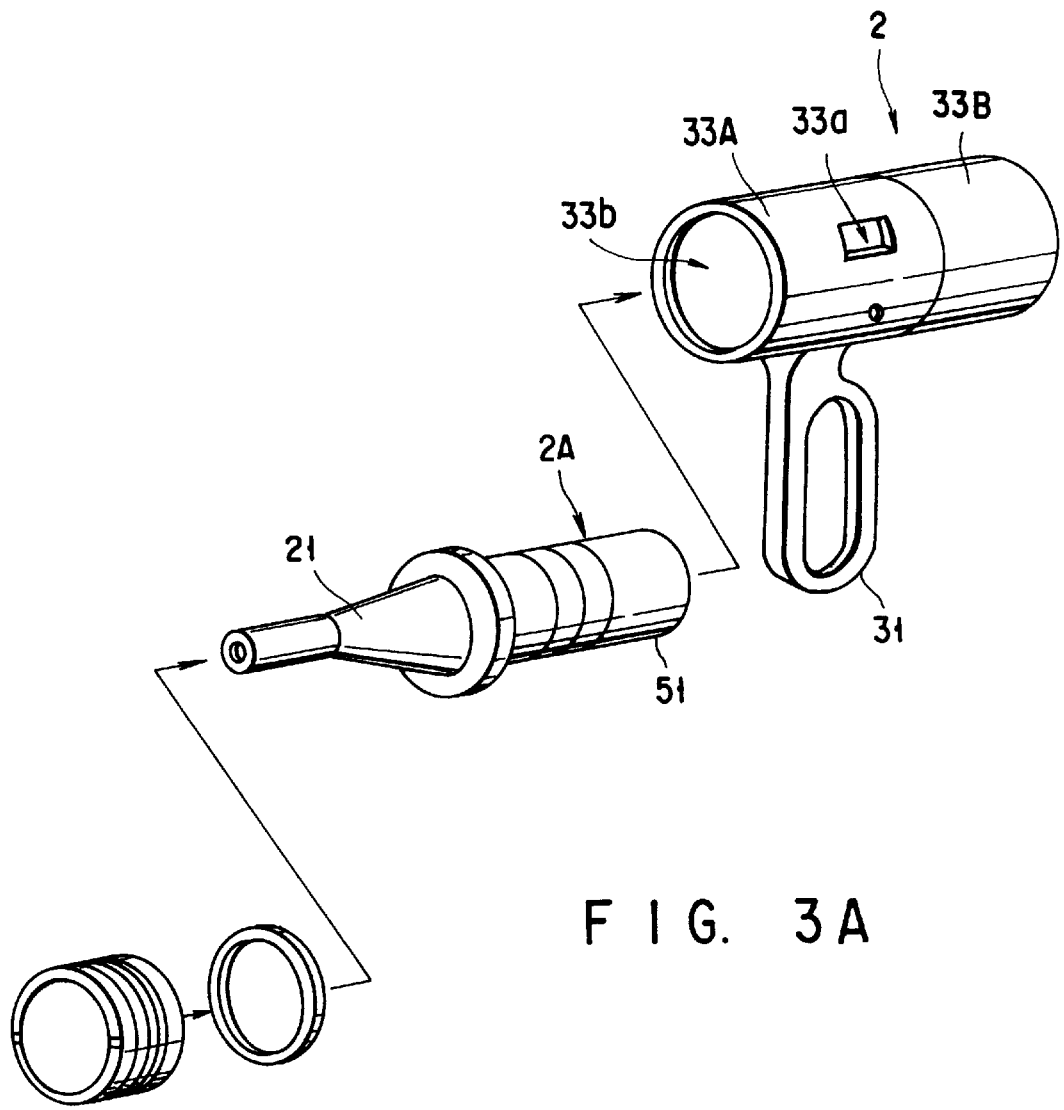
F I G. 3A
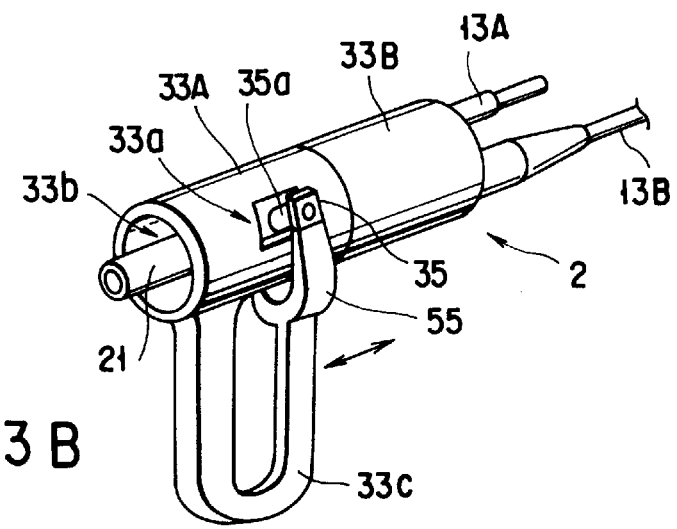
F I G. 3B

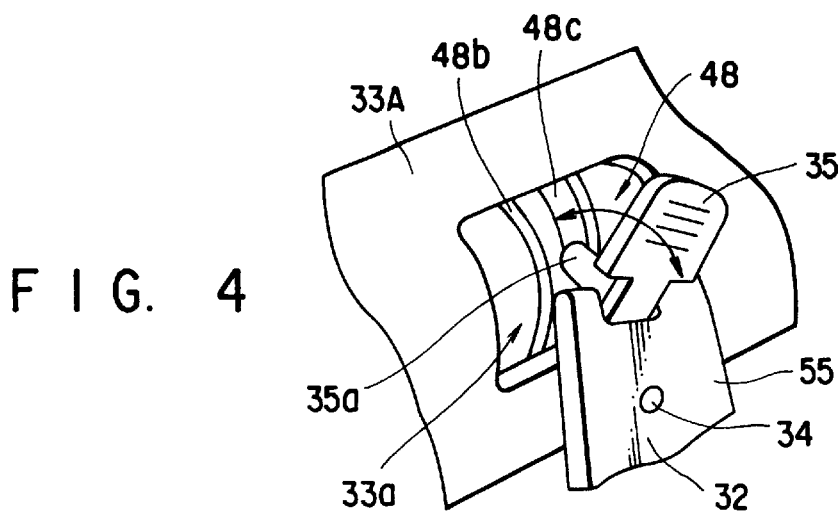
FIG. 4
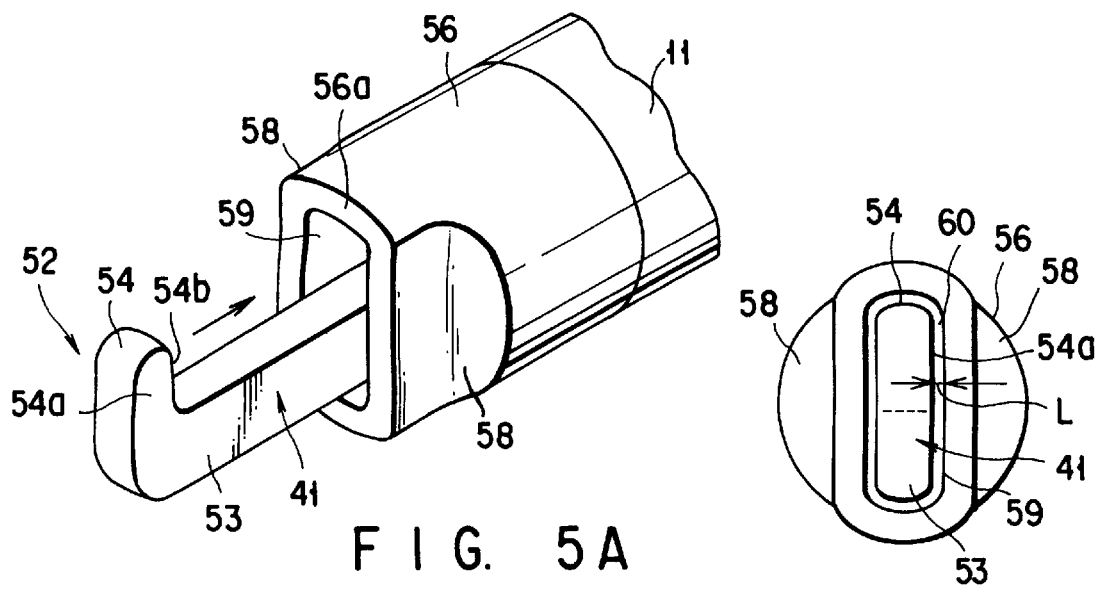
FIG. 5A
FIG. 5C
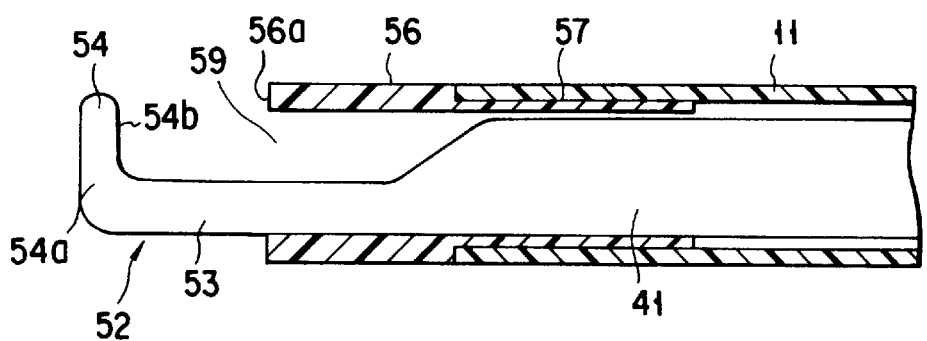
FIG. 5B

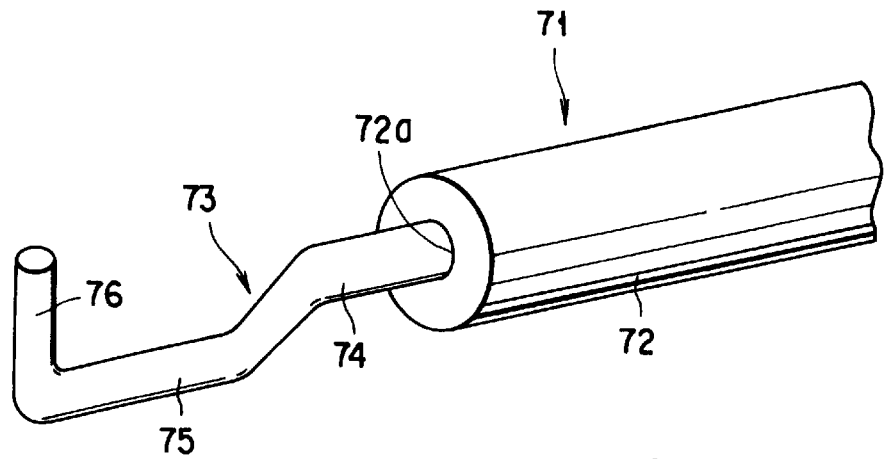
F I G. 10
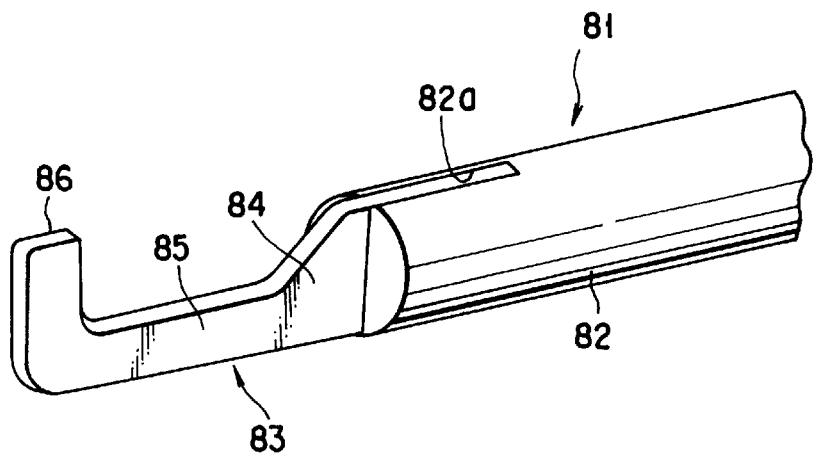
F I G. 11
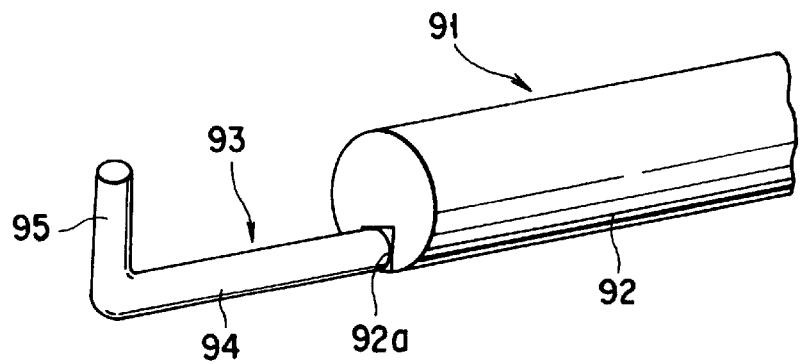
F I G. 12

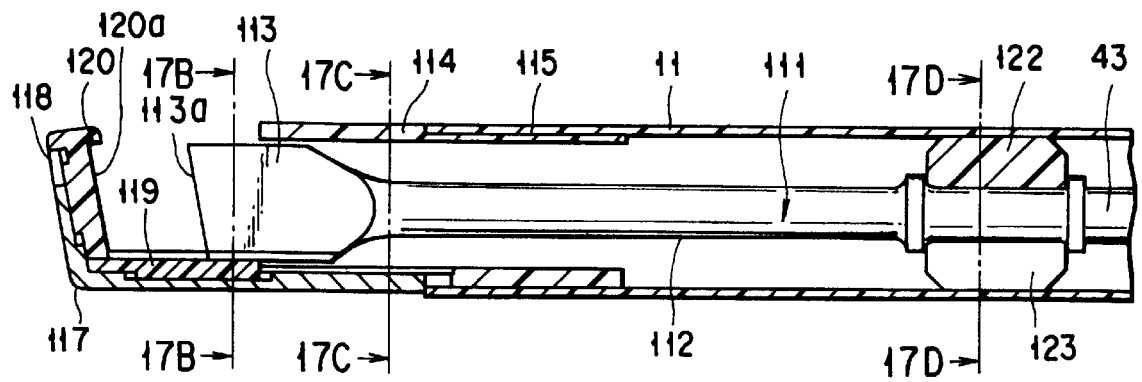
FIG. 17A
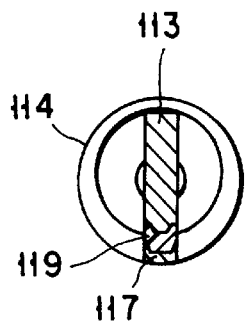 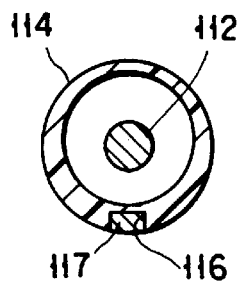 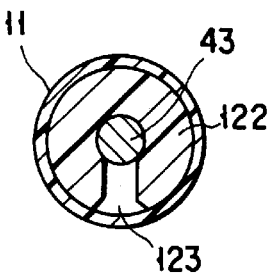
FIG. 17B      FIG. 17C      FIG. 17D
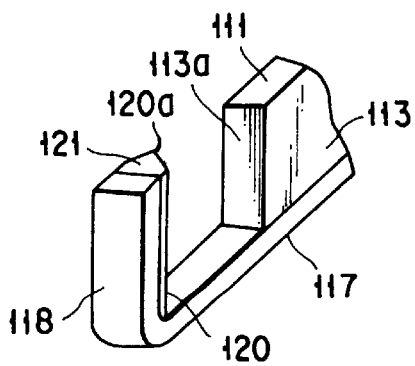 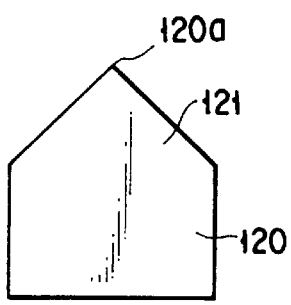 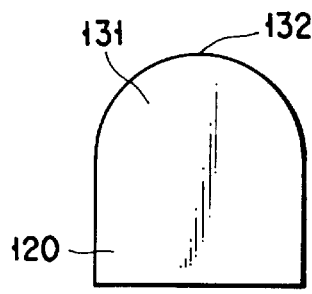
FIG. 18      FIG. 19A      FIG. 19B

ULTRASONIC TREATMENT INSTRUMENT

BACKGROUND OF THE INVENTION

This invention relates to an ultrasonic treatment instrument for performing treatments such as incision, excision, coagulation, etc.

U.S. Pat. No. 3,636,943, for example, discloses a general ultrasonic treatment instrument constructed as below. This ultrasonic treatment instrument comprises a substantially cylindrical sheath, and an ultrasonic probe mounted in the sheath such that it can slide along the axis of the sheath.

The sheath has, at its tip, a hook-shaped reception member of a substantially L shape. At the time of using the ultrasonic treatment instrument, the ultrasonic probe is slid relative to the sheath along the axis thereof, thereby holding an organic tissue such as a blood vessel between a tip portion of the probe and the hook-shaped reception member. Further, in this state, ultrasonic oscillation is transmitted to the tip portion of the probe, thereby subjecting the organic tissue held therebetween to an ultrasonic treatment such as a ligation thereof.

The instrument of U.S. Pat. No. 3,636,943 has a structure in which ultrasonic oscillation is transmitted, in an ultrasonic treatment, to the tip portion of the ultrasonic probe, and not to the hook-shaped reception member at the tip of the sheath. In other words, the hook-shaped reception member is kept still. This means that it is difficult for this instrument to peel a thin organic tissue using the hook-shaped reception member since the thin tissue may well slip from the reception member.

Moreover, U.S. Pat. No. 5,322,055, for example, discloses an ultrasonic treatment instrument with a structure in which a soft contact member for absorbing noise is attached to a hook-shaped reception member provided at the tip of a sheath. In this case, however, it is impossible at the tip of the hook-shaped member to perform peeling, etc. of an organic tissue using ultrasonic oscillation, or to perform a treatment using high frequency current. Thus, it is difficult to impart many functions to the ultrasonic treatment instrument.

BRIEF SUMMARY OF THE INVENTION

The present invention has been developed under the above-described circumstances, and aims to provide a multi-functional ultrasonic treatment instrument capable of performing various simple treatments such as peeling of an organic tissue, etc.

To attain the aim, there is provided an ultrasonic treating instrument for performing an ultrasonic treatment of an organic tissue comprising: an ultrasonic transducer for generating ultrasonic oscillation; a hand piece containing the ultrasonic transducer; a probe having a proximal end portion connected to the ultrasonic transducer and a distal end portion to be brought into contact with an organic tissue, the probe transmitting the ultrasonic oscillation of the ultrasonic transducer to the distal end thereof; a sheath covering the probe and having a front end portion extending toward the distal end portion of the probe, and a rear end portion connected to the hand piece; a hook-shaped treatment section provided at the distal end portion of the probe for performing a treatment of an organic tissue, the sheath having an axis and a hook portion bent substantially perpendicular to the axis; and operation means for moving the sheath and the probe relative to each other along the axis of the sheath, thereby holding an organic tissue between the hook-shaped treatment section of the probe and the front end portion of the sheath.

At the time of using the ultrasonic treatment instrument, the sheath and the probe are moved relative to each other along the axis of the sheath, thereby holding an organic tissue between the treatment section of the probe and the front end portion of the sheath. In this state, ultrasonic oscillation is applied to the treatment section of the probe to perform an ultrasonic treatment of the organic tissue therebetween, such as a ligation of a blood vessel. Further, while the ultrasonic oscillation is applied to the hook-shaped treatment section of the probe, a tip portion of the treatment section of the probe is pressed against an organic tissue in the form, for example, of a film, thereby preventing the organic tissue film from slipping therefrom. As a result, peeling, etc. of the organic tissue film can be performed easily.

As described above, the invention provides a multi-functional ultrasonic treatment instrument capable of performing various simple treatments such as peeling of an organic tissue, etc.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, servo to explain the principles of the invention.

FIG. 2A is a side view partly in section, showing an exploded state of a probe incorporated in the instrument of the first embodiment;

FIG. 2B is a side view, showing a state in which the probe is coupled with a hook-shaped treatment section in the instrument of the first embodiment;

FIG. 2C is a side view partly in section, showing a connecting section incorporated in a modification of the probe in the first embodiment;

FIG. 3A is an exploded perspective view, showing a hand piece incorporated in the first embodiment;

FIG. 3B is a perspective view, showing the assembled state of the hand piece in a modification of the first embodiment;

FIG. 4 is a view, useful in explaining an example of a state in which an operating section and a rotor incorporated in the first embodiment are engaged with each other;

FIG. 5A is a perspective view, showing an essential part of the hook-shaped treatment section and a sheath incorporated in the first embodiment, and useful in explaining the relationship therebetween;

FIG. 5B is a longitudinal sectional view, useful in explaining the relationship between the hook-shaped treatment section and the sheath of the first embodiment;

FIG. 5C is a front view, showing an essential part of the hook-shaped treatment section and a sheath incorporated in the first embodiment;

FIG. 10 is a perspective view, showing a hook-shaped treatment section incorporated in a fifth embodiment;

FIG. 11 is a perspective view, showing a hook-shaped treatment section incorporated in a sixth embodiment;

FIG. 12 is a perspective view, showing a hook-shaped treatment section incorporated in a seventh embodiment;

FIG. 17A is a longitudinal sectional view of an essential part of the tenth embodiment, useful in explaining the relationship between a front end treatment section of the probe and a front end pressing portion of the sheath;

FIG. 17B is a sectional view, taken along lines 17B—17B of FIG. 17A;

FIG. 17C is a sectional view, taken along lines 17C—17C of FIG. 17A;

FIG. 17D is a sectional view, taken along lines 17D—17D of FIG. 17A;

FIG. 18 is a perspective view, showing the front end treatment section of the probe and the front end pressing portion of the sheath in the tenth embodiment;

FIG. 19A is a perspective view, showing an elastic member attached to the front end pressing portion of the sheath in the tenth embodiment;

FIG. 19B is a plan view, showing a modification of the elastic member of the front end pressing portion in the tenth embodiment;

DETAILED DESCRIPTION OF THE INVENTION

Figure 1:
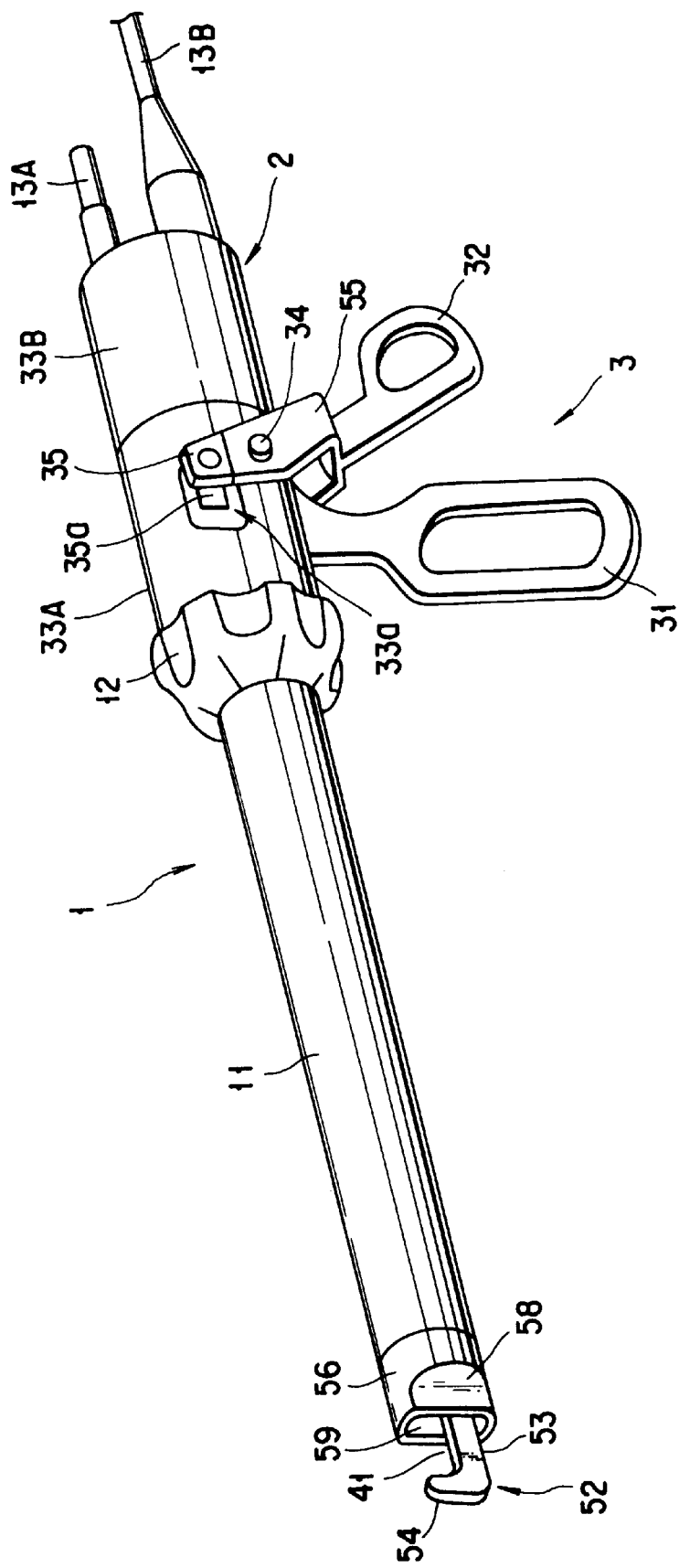
FIG. 1 is a schematic perspective view, showing the overall structure of an ultrasonic incising/coagulating instrument according to a first embodiment of the invention.

The first embodiment of the invention will be described with reference to FIGS. 1–6. FIG. 1 is a schematic perspective view, showing the overall structure of an ultrasonic incising/coagulating instrument of the first embodiment. As is shown in FIG. 1, a main body (instrument main body) 1 employed in the ultrasonic incising/coagulating instrument comprises an elongated cylindrical sheath 11 as a protection member. A hand piece 2 is attached to a proximal end portion of the sheath 11. The hand piece 2 contains an ultrasonic transducer 51 (see FIGS. 2A and 2B) for generating ultrasonic oscillation. The hand piece 2 comprises a cylindrical stationary cylinder section 33A and a cylindrical transducer cover 33B located behind the stationary cylinder section 33A. A tip portion of the transducer cover 33B is rotatably coupled with a rear end portion of the stationary cylinder section 33A. The ultrasonic transducer 51 is contained in the transducer cover 33B.

The hand piece 2 also comprises an operating section (operating means) 3 which includes a stationary handle 31 and a movable handle 32. The stationary handle 31 is formed integral with the stationary cylinder section 33A of the hand piece 2. A window 33a is formed in a side portion of the stationary cylinder section 33A. An electrode plug 13A projects from the rear end of the hand piece 2, and an electric cord 13B is connected to the rear end. The electrode plug 13A is arranged to be connected, via a connection cord (not shown), to a power supply for a high frequency treatment dedicated to an electric surgical knife, etc. Furthermore, the electric cord 13B is connected to a driving power supply for the ultrasonic transducer 51.

The sheath 11 contains a probe 52 shown in FIGS. 2A and 2B. The probe 52 transmits ultrasonic oscillation from the ultrasonic transducer 51, to a tip portion of the main body 1. The probe 52 comprises a horn 21 connected to the ultrasonic transducer 51, an oscillation transmitting rod 43 and a hook-shaped treatment section 41 for treating an organic tissue. The probe 52 and the ultrasonic transducer 51 constitute a transducer unit 2A. When the transducer unit 2A operates, oscillation generated from the ultrasonic transducer 51 is transmitted to the hook-shaped treatment section 41 via the horn 21 and the oscillation transmitting rod 43. At this time, the hook-shaped treatment section 41 constituting a tip portion of the probe 52 is brought into contact with an organic tissue to thereby perform an ultrasonic treatment of the tissue.

The electrode plug 13A shown in FIG. 1 is connected to the probe 52 via a lead wire (not shown). The probe 52 is supplied with a high frequency current, when necessary. When the hook-shaped treatment section 41 of the probe 52 is brought into contact with an organic tissue, with the high frequency current supplied thereto, it is used as an electric surgical knife and performs a high frequency treatment of the organic tissue.

A substantially L-shaped hook 54 formed e.g. by milling constitutes a tip portion of the axial body 53 of the hook-shaped treatment section 41. The hook 54 is bent in a direction substantially perpendicular to the axis of the sheath 11. The hook-shaped treatment section 41 is made of titanium, aluminum, an alloy of titanium or aluminum, etc. which shows a high acoustic effect and a high adaptability to organism.

Male screw portions 43c and 43d are provided on the opposite ends of the oscillation transmitting rod 43, respectively. A screw hole (not shown) for receiving the male screw 43c is formed in the proximal end of the hook-shaped treatment section 41, while a screw hole (not shown) for receiving the male screw 43d is formed in the distal end of the horn 21. As a result, the proximal end of the hook-shaped treatment section 41 and the distal end of the horn 21 are detachably screwed in the distal end and proximal end of the oscillation transmitting rod 43, respectively.

Instead of the above, female screws 43e and 43f may be formed in opposite end portions of the oscillation transmitting rod 43, as is shown in FIG. 2C. In this case, male screws 41a and 21a to be engaged with the female screws 43e and 43f are formed in the proximal end of the hook-shaped treatment section 41 and the distal end of the horn 21, respectively.

Each element of the probe 52 for transmitting oscillation from the ultrasonic transducer 51 is made of titanium, aluminum, an alloy of titanium or aluminum, etc. which shows a high acoustic effect and a high adaptability to organism. In this embodiment, the hook-shaped treatment section 41 and the horn 21 for transmitting ultrasonic oscillation from the ultrasonic transducer, to the oscillation transmitting rod 43 are formed of titanium which has a high durability. On the other hand, the oscillation transmitting rod 43 which serves as a relay member connecting the horn 21 to the hook-shaped treatment section 41 is formed of cheap aluminum.

As is shown in FIG. 3A, the ultrasonic transducer 51 is contained in a hole 33b formed in the hand piece 2 such that it can slide axially. The transducer 51 is connected to a tubular rotor 48 shown in FIG. 4 and serving as connecting means. The rotor 48 is axially slidably inserted in the hole 33b.

As is shown in FIG. 1, a substantially U-shaped coupling arm 55 constitutes an upper portion of the movable handle 32. A vertically substantially center portion of the coupling arm 55 is attached to the stationary cylinder section 33A such that it can pivot about a handle support pin 34.

An engagement member 35 clearly shown in FIG. 4 is attached to the upper end of the coupling arm 55 of the handle 32. The engagement member 35 is rotatably coupled with the coupling arm 55 toward the axis of the stationary cylinder section 33A which is viewed through the window 33a of the section 33A. The engagement member 35 has a projecting engagement claw 35a detachably engaged with the rotor 48 in the hand piece 2.

A projection 48b projects from a center portion of the rotor 48 such that it can slide on the wall which defines the hole 33b in the hand piece 2. The projection 48a has a groove 48c formed therein with which the engagement claw 35a of the movable handle 32 is engaged. The overall transducer unit 2A is retreated when the movable handle 32 is moved toward the stationary handle 31. At this time, the hook 54 of the hook-shaped treatment section 41 moves toward the open end 58 of a reception member 56 provided at the tip of the sheath 11, which will be described later.

As is shown in FIG. 4, the rotor 48 can easily be detached from the hole 33b of the hand piece 2 by disengaging the engagement claw 35a of the movable handle 32 from the groove 48c of the rotor 48.

The first embodiment can be modified as shown in FIG. 3B in which an operation handle 33c obtained by forming the stationary handle 31 integral with the movable handle 32.

An annular rotary knob 12 is attached to the rear end (i.e. proximal end) of the sheath 11. The knob 12 is coupled integral with the sheath 11 and the transducer cover 33B. The transducer unit 2A can rotate relative to the stationary cylinder section 33A together with the transducer cover 33B and the sheath 11. The transducer cover 33B, the sheath 11 and the hook 54 are rotated all together by rotating the rotary knob 12.

The sheath 11 is made of a heat resistant and slippery material such as a fluorocarbon resin (e.g. Teflon). The sheath 11 may be made of polyacetal or polyethylene.

As is shown in FIGS. 5A and 5B, a substantially cylindrical reception member 56 is fixed to the distal end of the sheath 11 and serves as protection means for preventing the oscillation transmitting rod 43 from being brought into direct contact with the inner peripheral surface of the sheath 11. The reception member 56 is made of a fluorocarbon resin with a high sliding property (e.g. Teflon). The inner diameter of the reception member 56 is set smaller than the inner diameter of the sheath 11 as shown in FIG. 5B.

The reception member 56 has an annular rear end portion 57 having an outer diameter smaller (hereinafter referred to as a "small-diameter portion" 57) than a front portion thereof. The outer diameter of the small-diameter portion 57 is substantially identical to the inner diameter of the sheath 11. The small-diameter portion 57 is press-fitted in the sheath 11.

The reception member 56 has a tapered restriction portion 58 at its front end as shown in FIGS. 5A and 5C. The restriction portion 58 has an open front end 59 with the shape of a substantial ellipse, which substantially corresponds to the shape of a front end portion of the hook 54 of the hook-shaped treatment section 41.

Figure 6:
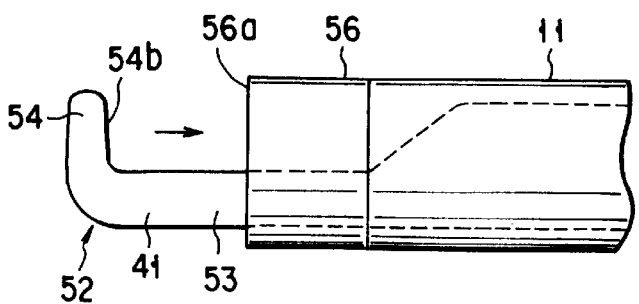
FIG. 6 is a side view, useful in explaining the operation of the hook-shaped treatment section of the first embodiment.

The hook 54 of the hook-shaped treatment section 41 is supported by the sheath 11 such that it projects outward from the open front end 59 of the restriction portion 58. As is shown in FIG. 6, the end face 54b of the hook 54 opposed to the reception member 56 of the sheath 11 is arranged exactly perpendicular to the axis of the sheath 11. Similarly, the end face 56a of the reception member 56 opposed to the hook 54 is arranged exactly perpendicular to the axis of the sheath 11. An organic tissue is to be held between the end face 54b of the hook 54 of the hook-shaped treatment section 41 and the end face 56a of the reception member 56.

As is shown in FIG. 5C, a clearance 60 of a predetermined width L is defined between the inner edge of the front open end 59 of the restriction portion 58 and the wear face 54a of one side of the hook 54. The width of the clearance 60 can be set to any voluntary value in accordance with the coagulating force of the instrument. When the movable handle 32 is moved toward the stationary handle 31, the overall probe 52 moves toward the proximal end of the instrument as indicated by the arrows in FIGS. 5A and 6. While the overall probe 52 is thus moved, an organic tissue is held between the treatment section 41 of the probe 52 and the edge of the front open end 59 of the sheath 11. At this time, part of the organic tissue is held in the clearance 60 between the inner edge of the front open end 59 and the wear face 54a of the one side of the hook 54, and is ground by the wear face. In this state, the organic tissue is removed.

The operation of the ultrasonic incising/coagulating instrument constructed as above will be described, taking, as an example, a case where the main body 1 of the ultrasonic incising/coagulating instrument is inserted in an abdominal cavity.

First, the tip of the main body 1 is moved to a target organic tissue. Subsequently, the movable handle 32 of the operating section 3 is moved toward the stationary handle 31, thereby clockwise rotating, about the handle support pin 34, the engagement claw 35a of the engagement member 35 of the movable handle 32 as shown in FIG. 1. Accordingly, the rotor 48 is pulled rearward by the engagement claw 35a along the axis of the sheath 11. As a result, the overall transducer unit 2A is moved rearward together with the rotor 48.

While the probe 52 is further moved toward the proximal end of the instrument as indicated by the arrows shown in FIGS. 5A and 6, an organic tissue is held between the hook 54 of the front end treatment section 41 of the probe 52 and the edge of the front open end 59 of the restriction portion 58 of the front end reception member 56 of the sheath 11. At this time, part of the organic tissue is held in the clearance 60 between the inner edge of the front open end 59 of the restriction portion 58 and the wear face 54a of one side of the hook 54, and is ground by the wear face.

In this state, the ultrasonic transducer 51 in the hand piece 2 is driven by a power supplied from an ultrasonic transducer driving power supply, thereby generating an ultrasonic wave. The oscillation of the ultrasonic wave generated from the ultrasonic transducer 51 is transmitted to the hook-shaped treatment section 41 via the horn 21 and the oscillation transmitting rod 43. The ultrasonic oscillation is then transmitted to the organic tissue held between the hook 54 of the treatment section 41 and the reception member 56 of the sheath 11, thereby coagulating the same by frictional heat due to the oscillation.

While the ultrasonic oscillation is applied to the organic tissue, the movable handle 32 is further moved toward the stationary handle 31 to increase the force of holding of the tissue. Accordingly, the hook 54 of the treatment section 41 further approaches the reception member 56, with the result that the organic tissue is excised without bleeding.

Moreover, peeling an organic tissue in the form of a film, for example, can be performed by bringing the tip of the hook 54 of the treatment section 41 of the probe 52 into contact with the tissue film, with the ultrasonic oscillation applied to the hook-shaped treatment section 41. Since at this time, the tip of the hook-shaped treatment section of the probe which contacts the tissue film is oscillated by the ultrasonic oscillation, the tissue film is prevented from slipping from the hook-shaped treatment section. Thus, the tissue film can easily be peeled.

In addition, supplying a high frequency current to the probe 52 enables the use of the probe 52 as an electric surgical knife for performing a high frequency treatment of an organic tissue.

The above-described ultrasonic incising/coagulating instrument provides the following advantage:

Since the hook-shaped treatment section 41 which is bent perpendicular to the axis of the sheath 11 constitutes a front end portion of the probe 52, a single ultrasonic incising/coagulating instrument can perform various treatments as described above, i.e. the ultrasonic treatment in which an organic tissue held between the hook-shaped treatment section 41 of the probe 52 and the reception member 56 of the sheath 11, e.g. a blood vessel, is ligated; the ultrasonic treatment in which the tip of the hook 54 of the treatment section 41 to which ultrasonic oscillation is applied is brought into contact with, for example, a tissue film to peel the tissue film off; or the high frequency treatment in which the hook-shaped treatment section 41 of the probe 52 is used as an electric surgical knife when it is supplied with a high frequency current. Thus, the single ultrasonic incising/coagulating instrument of the first embodiment can be used for much more purposes and hence is much more convenient than the conventional instrument.

Furthermore, in the above embodiment, at the time of performing a high frequency treatment of an organic tissue, a high frequency current is supplied to the probe 52 while ultrasonic oscillation is applied to the hook-shaped treatment section 41 of the probe 52. Accordingly, an organic tissue burned by the high frequency current can be prevented from sticking to the probe 52. This can omit a complicated treatment performed after the high frequency treatment for removing a burned sticking tissue using a tool such as a file.

Since the sheath 11 is made of a heat resistant and slippery material such as a fluorocarbon resin (e.g. Teflon), the sheath 11 will not melt even if a frictional heat is generated between the sheath 11 and the probe 52 where the inner peripheral surface of the sheath 11 contacts the oscillating probe 52. Therefore, it is not necessary to provide a large clearance between the inner peripheral surface of the sheath 11 and the oscillating probe 52. Accordingly, the sheath 11 can be made small in outer diameter, which is advantageous in producing a thin ultrasonic incising/coagulating instrument.

Also, since the inner diameter of the reception member 56 attached to the front end of the sheath 11 is set smaller than the inner diameter of the sheath 11, that portion of the reception member 56 which projects in the sheath 11 functions as a spacer for preventing the oscillating probe 52 from easily contacting the inner peripheral surface of the sheath 11.

Furthermore, the tapered restriction portion 58 constituting the tip of the reception member 56 can reduce the area of that portion of the field of endoscopic view which is situated around and interrupted by the tip of the sheath 11. This means that the restriction portion 58 can provide a relatively large field of endoscopic view.

Since the clearance 60 of the predetermined width L corresponding to the force of coagulation of the instrument is defined between the inner edge of the front open end 59 of the restriction portion 58 of the reception member 56 and the wear face 54a of one side of the hook 54, as is shown in FIG. 5C, an organic tissue is held between the treatment section 41 of the probe 52 and the edge of the front open end 59 of the restriction portion 58 of the reception member 56, and part of the organic tissue is held in the clearance 60 between the inner edge of the front open end 59 and the wear face 54a of the one side of the hook 54, and is ground by the wear face. The organic tissue part held in the clearance 60 can securely be coagulated.

A more efficient treatment can be performed by exchanging, if necessary, the hook-shaped treatment section 41 screwed in the front end of the oscillation transmitting rod 43, with another one of a configuration or a size more suitable to the treatment or with another one capable of performing a more suitable surface treatment. A similar function or advantage can be attained by providing the rotor 48 with a convex portion and the operating section 3 with a concave portion.

Although in the first embodiment, the sheath 11 is formed of a fluorocarbon resin tube, it may be formed of a metal tube with its inner peripheral surface coated with a heat resistant and slippery material such as Teflon.

Further, although in the first embodiment, the reception member 56 as a separate member is fixed to the front end of the sheath 11, the former may be formed integral as one body with the latter.

Figure 7:
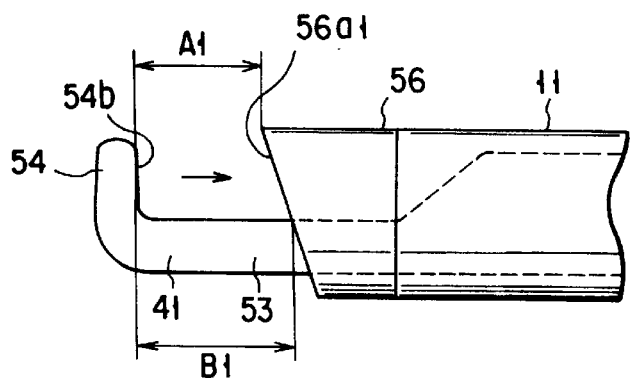
FIG. 7 is a side view, showing a hook-shaped treatment section incorporated in a second embodiment.

Referring then to FIG. 7, an ultrasonic incising/coagulating instrument according to a second embodiment will be described. This embodiment differs from the first embodiment (shown in FIGS. 1–6) in the structure of the reception member 56.

The reception member 56 incorporated in the second embodiment has an inclined end face 56a1 opposed to the inner end face 54b of the hook 54. The end face 56a1 inclines such that an upper portion thereof is closer to the inner end face 54b of the hook 54 of the hook-shaped treatment section 41 than a lower portion thereof in FIG. 7. In other words, the inclination angle of the inclined end face 56a1 with respect to the line perpendicular to the axis of the sheath 11 is more than 0°. As a result, the distance A1 between the upper portion of the inclined end face 56a1 and an upper portion of the inner end face 54b of the hook 54 is narrower than the distance B1 between the lower portion of the inclined end face 56a1 and a lower portion of the inner end face 54b of the hook 54.

An organic tissue held between the inclined end face 56a1 of the reception member 56 and the inner end face 54b of the hook 54 does not easily slip therefrom.

Figure 8:
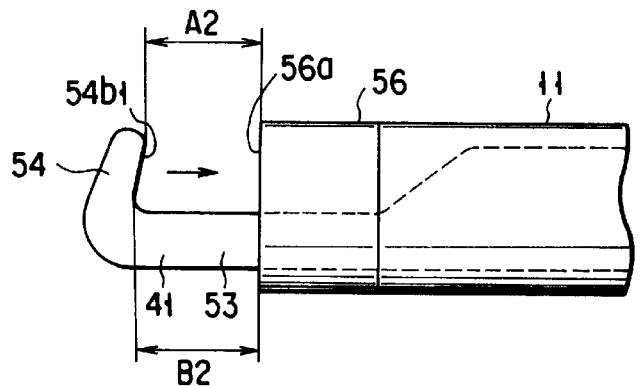
FIG. 8 is a side view, showing a hook-shaped treatment section incorporated in a third embodiment.

Referring to FIG. 8, an ultrasonic incising/coagulating instrument according to a third embodiment will be described. This embodiment differs from the first embodiment (shown in FIGS. 1–6) in the structure of the hook-shaped treatment section 41.

The hook 54 of the hook-shaped treatment section 41 incorporated in the third embodiment has an inclined end face 54b1 opposed to the reception member 56. The end face 54b1 inclines such that an upper portion thereof is closer to the end face 56a of the reception member 56 than a lower portion thereof. In other words, the inclination angle of the inclined end face 54b1 with respect to the line perpendicular to the axis of the sheath 11 is more than 0°. As a result, the distance A2 between the upper portion of the inclined end face 54b1 and an upper portion of the end face 56a of the reception member 56 is narrower than the distance B2 between the lower portion of the inclined end face 54b1 and a lower portion of the end face 56a of the reception member 56.

An organic tissue held between the inclined end face 54b1 of the hook 54 and the end face 56a of the reception member 56 does not easily slip therefrom.

Figure 9:
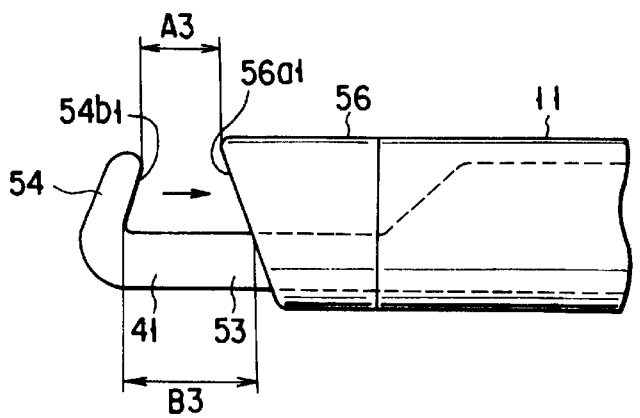
FIG. 9 is a side view, showing a hook-shaped treatment section incorporated in a fourth embodiment.

Referring then to FIG. 9, an ultrasonic incising/coagulating instrument according to a fourth embodiment will be described. This embodiment differs from the first embodiment (shown in FIGS. 1–6) in the structures of the hook-shaped treatment section 41 and the reception member 56.

In this embodiment, the reception member 56 has an inclined end face 56a1 opposed to the hook 54 of the hook-shaped treatment section 41 as in the case of the second embodiment (shown in FIG. 7), and the hook 54 of the hook-shaped treatment section 41 has an inclined end face 54b1 opposed to the reception member 56 as in the case of the third embodiment (shown in FIG. 8). As a result, the distance A3 between an upper portion of the inclined end face 56a1 of the reception member 56 and an upper portion of the inclined end face 54b1 of the hook 54 is much narrower than the distance B3 between lower portions of them. By virtue of this structure, an organic tissue can be held by the instrument more securely than in the case of the second and third embodiments.

FIG. 10 shows an essential part of an ultrasonic incising/coagulating instrument according to a fifth embodiment. This embodiment differs from the first embodiment (shown in FIGS. 1–6) in that the former employs a hook-shaped treatment section 71 constructed as below instead of the hook-shaped treatment section 41.

The hook-shaped treatment section 71 has an axial member 72 and a substantially L-shaped, bent wire member 73. The axial member 72 has a center hole 72a formed in the front end face thereof. A proximal end portion of the wire member 73 is fitted and fixed in the center hole 72a.

The bent wire member 73 comprises a fixed portion 74, a bent portion 75 and a hook portion 76. The fixed portion 74 is inserted and fixed in the center hole 72a of the axial member 72. The bent portion 75 extends from the fixed portion 74 in a direction eccentric to the axis of the axial member 72. The hook portion 76 extends from the bent portion 75 in a direction substantially perpendicular to the axis of the sheath 11.

As described above, the hook-shaped treatment section 71 comprises two components, i.e. the linearly extending axial member 72 and the wire member 73 fixed thereto, and the wire member 73 has the substantially L-shaped hook portion 76. This means that in this embodiment, it suffices if at least the wire member 73 is made of expensive titanium with a high adaptability to an organism, and the axial member 72 may be made of a cheaper material. Accordingly, the hook-shaped treatment section 71 and hence the probe 52 can be produced at a lower cost than in the first embodiment which employs the hook-shaped treatment section 41 produced by milling, into the substantially L-shaped hook 54, a tip portion of the axial body 53 made of expensive titanium showing a high acoustic effect and a high adaptability to an organism.

Moreover, in the fifth embodiment, the wire member 73 is secured to the axial member 72 by fitting the proximal end of the wire member 73 in the center hole 72a of the axial member 72. This means that the wire member 73 can be positioned easily with respect to the axial member 72, and hence that the hook-shaped treatment section 71 can be assembled easily.

FIG. 11 shows an essential part of an ultrasonic incising/coagulating instrument according to a sixth embodiment. This embodiment differs from the first embodiment (shown in FIGS. 1–6) in that the former employs a hook-shaped treatment section 81 constructed as below instead of the hook-shaped treatment section 41.

The hook-shaped treatment section 81 has an axial member 82 and a substantially L-shaped plate member 83 formed by cutting. The axial member 82 has a linear slot 82a formed in a front end portion thereof. A proximal end portion of the plate member 83 is fitted and fixed in the linear slot 82a.

The plate member 83 comprises a fixed portion 84, an eccentric portion 85 and a hook portion 86. The fixed portion 84 is inserted and fixed in the linear slot 82a of the axial member 82. The eccentric portion 85 extends from the fixed portion 84 in a direction eccentric to the axis of the axial member 82. The hook portion 86 extends from the eccentric portion 85 in a direction substantially perpendicular to the axis of the sheath 11.

As described above, the hook-shaped treatment section 81 comprises two components, i.e. the linearly extending axial member 82 and the plate member 83 fixed thereto, and the plate member 83 has the substantially L-shaped hook portion 86. This means that in this embodiment, it suffices if at least the plate member 83 is made of expensive titanium with a high adaptability to an organism, and the axial member 82 may be made of a cheaper material. Accordingly, the hook-shaped treatment section 81 and hence the probe 52 can be produced at a lower cost than in the first embodiment which employs the hook-shaped treatment section 41 produced by milling, into the substantially L-shaped hook 54, a tip portion of the axial body 53 made of expensive titanium showing a high acoustic effect and a high adaptability to an organism.

FIG. 12 shows an essential part of an ultrasonic incising/coagulating instrument according to a seventh embodiment.

This embodiment differs from the first embodiment (shown in FIGS. 1–6) in that the former employs a hook-shaped treatment section 91 constructed as below instead of the hook-shaped treatment section 41.

The hook-shaped treatment section 91 has an axial member 92 and a substantially L-shaped, bent wire member 93. The axial member 92 has a linear attachment groove 92a axially formed in a peripheral front end portion thereof. A proximal end portion of the wire member 93 is fitted and fixed in the attachment groove 92a.

The wire member 93 comprises a fixed portion 94 and a hook portion 95. The fixed portion 94 is inserted and fixed in the attachment groove 92a of the axial member 92. The hook portion 95 extends from the fixed portion 95 in a direction substantially perpendicular to the axis of the sheath 11.

As described above, the hook-shaped treatment section 91 comprises two components, i.e. the linearly extending axial member 92 and the wire member 93 fixed thereto, and the wire member 93 has the substantially L-shaped hook portion 95. This means that also in this embodiment, it suffices if at least the wire member 93 is made of expensive titanium with a high adaptability to an organism, and the axial member 92 may be made of a cheaper material. Accordingly, the hook-shaped treatment section 91 and hence the probe 52 can be produced at a lower cost than in the first embodiment which employs the hook-shaped treatment section 41 produced by milling, into the substantially L-shaped hook 54, a tip portion of the axial body 53 made of expensive titanium showing a high acoustic effect and a high adaptability to an organism.

Figure 13:
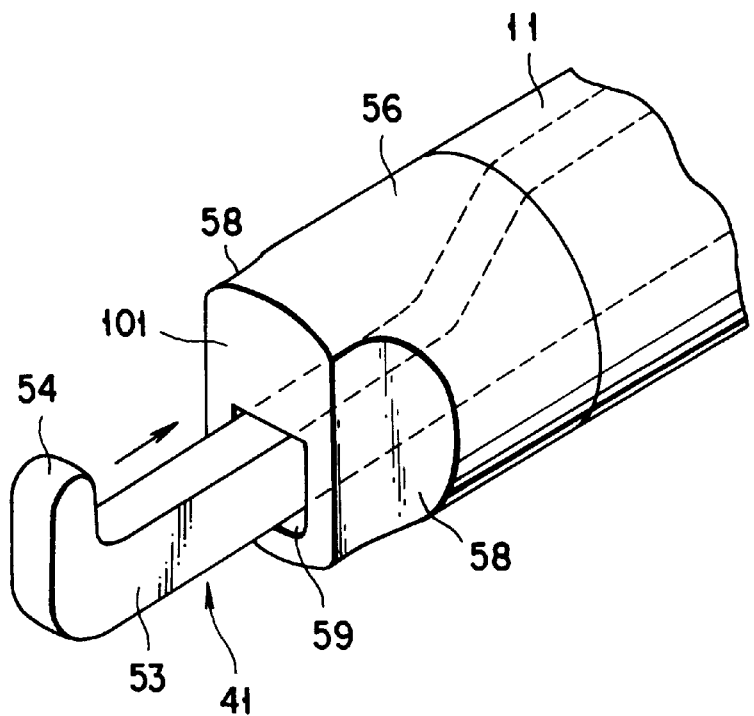
FIG. 13 is a perspective view, showing the relationship between a hook-shaped treatment section and a sheath incorporated in an eighth embodiment.

Referring then to FIG. 13, an ultrasonic incising/coagulating instrument according to an eighth embodiment will be described. This embodiment differs from the first embodiment (shown in FIGS. 1–6) in the structure of the reception member 56.

In this embodiment, a pressing face 101 is provided at the opening 59 of the reception member 56. The pressing face 101 is formed by closing the part of the opening 59 which is opposed to the hook 54 of the hook-shaped treatment section 41.

The pressing face 101 increases the area of the reception member 56 which is brought into contact with an organic tissue. Accordingly, an organic tissue can be securely held between the end face 54b of the hook 54 and the pressing face 101 of the reception member 56.

Figure 14:
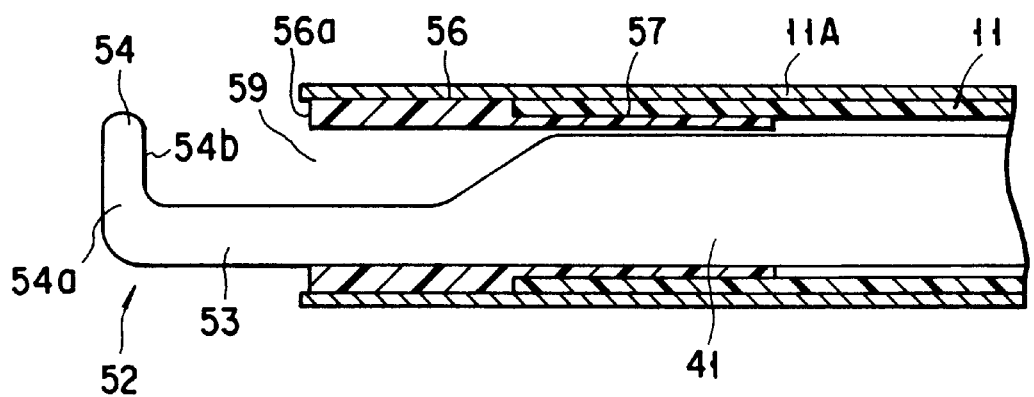
FIG. 14 is a longitudinal sectional view of an essential part of an instrument according to a ninth embodiment, showing a tip portion of a probe incorporated therein.

Referring then to FIG. 14, an ultrasonic incising/coagulating instrument according to a ninth embodiment will be described. This embodiment differs from the first embodiment (shown in FIGS. 1–6) in that an outer sheath 11A is additionally provided around the sheath 11.

The outer sheath 11A is axially slidable relative to the sheath 11.

Hence, even when in this embodiment, the probe 52 is axially moved at the time of opening or closing the movable handle 32 relative to the stationary handle 31, the movement of the probe 52 will not be transmitted to the outer sheath 11A via the sheath 11. This means that even where the outer sheath 11A is in tight contact with the wall of a cavity in an organism during use of the ultrasonic incising/coagulating instrument, it does not axially move relative to the sheath 11 when the movable handle 32 is opened or closed. As a result, the instrument can be operated in a stable manner, and hence an ultrasonic treatment can be performed with high accuracy.

The invention is not limited to the above embodiments. For example, in the embodiments, the probe 52 is moved toward the proximal end of the instrument at the time of operating the movable handle 32, thereby making the hook 54 push an organic tissue against the reception member 56 of the sheath 11 to hold the tissue therebetween. Instead of this, the probe 52 may be fixed in position at the time of operating the movable handle 32. In this case, the reception member 56 of the sheath 11 is moved toward the hook 54 of the probe 52.

FIGS. 15–19A show an ultrasonic incising/coagulating instrument according to a tenth embodiment. This embodiment differs from the first embodiment (shown in FIGS. 1–6) as follows:

In the tenth embodiment, the transducer unit 2A provided in the sheath 11 is secured to the stationary handle 31 of the hand piece 2. At the time of operating the movable handle 32, the sheath 11 is moved axially. In FIGS. 15–19A, elements similar to those in FIGS. 1–6 are denoted by corresponding reference numerals, and no explanation is given thereof.

Figure 16A:
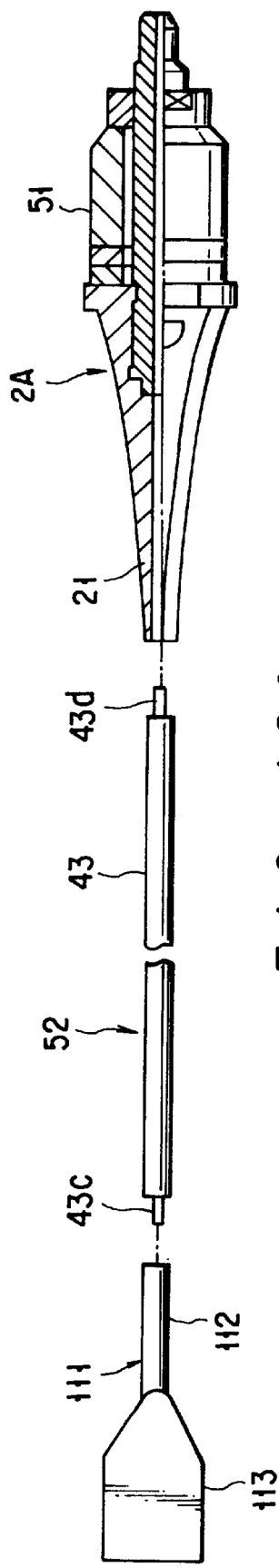
FIG. 16A is a side view, showing an exploded state of a probe incorporated in the instrument of the tenth embodiment.
Figure 16B:
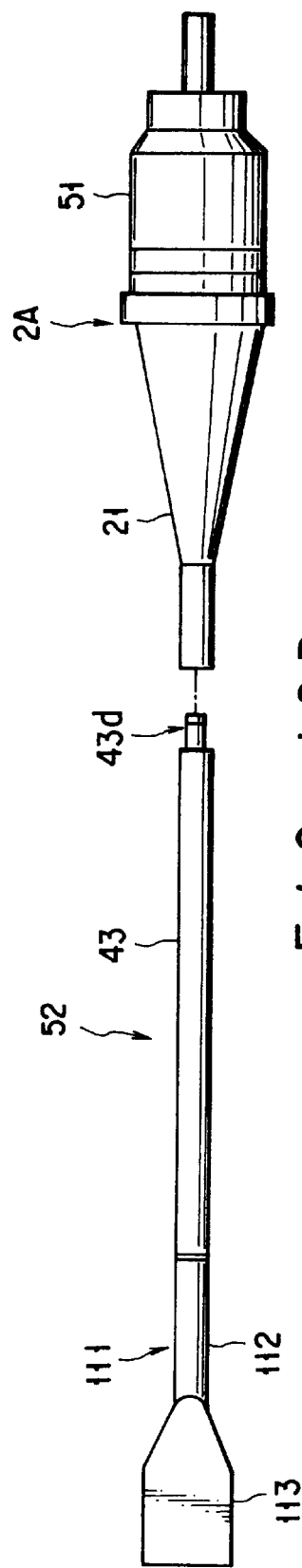
FIG. 16B is a side view, showing a state in which a front end treatment section and an oscillation transmitting rod incorporated in the probe of the tenth embodiment are coupled with each other.

As is shown in FIGS. 16A and 16B, a tip piece 111 which differs in structure from the hook-shaped treatment section 41 in the first embodiment is provided at a tip portion of the oscillation transmitting rod 43 of the probe 52. The tip piece 111 comprises an axial member 112 and a flat treatment section 113 attached to the front end of the axial member 112.

As is shown in FIG. 17A, the treatment section 113 has a front end with an inclined surface 113a, which inclines with respect to the line perpendicular to the axis of the sheath 11 such that an upper portion of the section 113 more projects than a lower portion thereof. The tip piece 111 is made of titanium, aluminum or an alloy of these materials, which shows a high acoustic effect and a high adaptability to an organism.

The tip piece 111 has a screw hole (not shown) formed in a proximal end portion thereof and engaged with the male screw 43c provided on the tip of the oscillation transmitting rod 43. Thus, the proximal end of the tip piece 111 is detachably engaged with the oscillation transmitting rod 43.

Figure 16C:
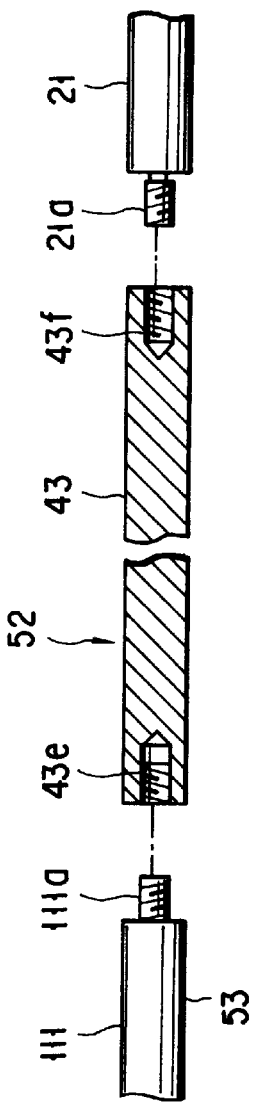
FIG. 16C is a view, useful in explaining engagement portions employed in a modification of the probe of the tenth embodiment.

Instead of the above structure, a female screw 43e may be formed in a tip portion of the oscillation transmitting rod 43, and a male screw 111a corresponding to the female screw 43e be formed in a proximal end portion of the tip piece 111, as is shown in FIG. 16C.

In the transducer unit 2A of the tenth embodiment, oscillation generated by the ultrasonic transducer 51 is transmitted to the tip piece 111 via the horn 21 and the oscillation transmitting rod 43, and an organic tissue is treated by the oscillated tip piece 111.

An electrode plug 13A is connected to the probe 52 by means of a lead wire (not shown). While the probe 52 is supplied with a high frequency current, the tip piece 111 of the probe 52 is brought into contact with an organic tissue to perform a high frequency treatment of the tissue.

The tip piece 111 and the horn 21 for transmitting ultrasonic oscillation to the transmitting rod 43 are made of titanium which has a high durability, and the transmitting rod 43 as a relay member connecting the horn 21 to the tip piece 111 is made of cheap aluminum.

A tip ring 114 is fixed to the distal end of the sheath 11 and serves as protection means for preventing the tip piece 111 of the probe 52 from being brought into direct contact with the inner peripheral surface of the sheath 11. The tip ring 114 is made of a fluorocarbon resin with a high sliding property (e.g. Teflon), and has an inner diameter smaller than the sheath 11 as shown in FIG. 17A.

The tip ring 114 has an annular rear end portion 115 having an outer diameter smaller (hereinafter referred to as a "small-diameter portion" 115) than a front end portion thereof. The outer diameter of the small-diameter portion 115 is substantially identical to the inner diameter of the sheath 11. The small-diameter portion 115 is press-fitted in the sheath 11.

Figure 15:
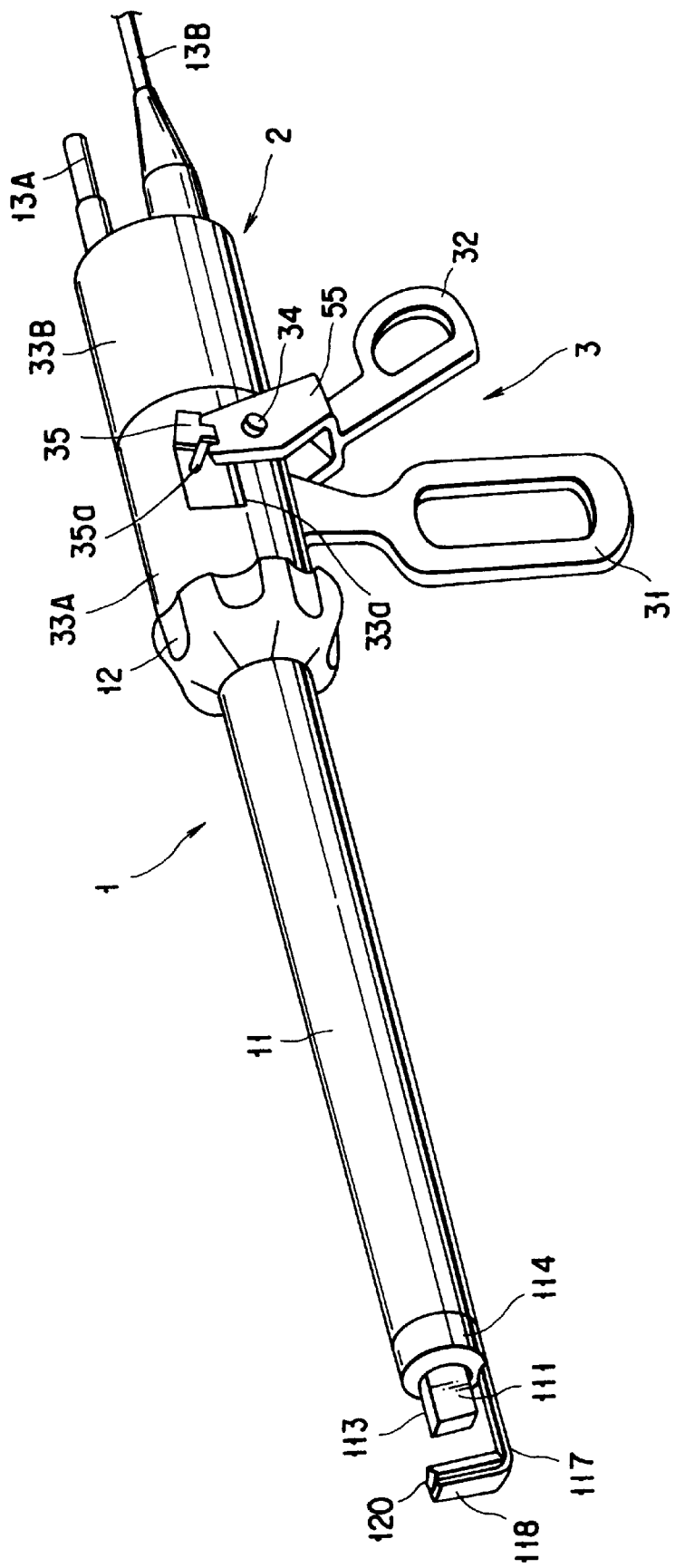
FIG. 15 is a schematic perspective view, showing an ultrasonic incising/coagulating instrument according to a tenth embodiment.

As is shown in FIGS. 17A and 17C, an axial linear attachment groove 116 is formed in the sheath 11, and securely receives a proximal end portion of a hook-shaped reception member 117 with a substantially L shape as shown in FIGS. 15 and 17A.

A front end portion of the reception member 117 constitutes a pressing portion 118 bent perpendicular to the axis of the sheath 11. The pressing portion 118 inclines relative to the line perpendicular to the axis of the sheath 11, i.e. it extends parallel to the inclined surface 113a of the tip piece 111.

Further, a first elastic member 119 is mounted on the lower surface portion of the reception member 117 which contacts the tip piece 111 of the probe 52. A second elastic member 120 is mounted on the portion of the pressing portion 118 which contacts the tip piece 111 of the probe 52. The first and second elastic members 119 and 120 are made of a heat resistant and slippery material such as a fluorocarbon resin (e.g. Teflon). These elastic members may be made of polyacetal or polyethylene.

As is shown in FIG. 19A, the second elastic member 120 of the pressing portion 118 has a prism-shaped projection 121 opposed to the tip piece 111 of the probe 52 as shown in FIG. 17A. The summit of the prism-shaped projection 121 is set to have an angle equal to or more than 90°. The summit of the prism-shaped projection 121 constitutes a contact portion 120a of a small area to be brought into contact with the inclined surface 113a of the tip piece 111. The contact portion 120a of the projection 121 is inclined parallel to the inclined surface 113a.

The second elastic member 120 of the pressing portion 118 may be modified as shown in FIG. 19B. In this case, the elastic member 120 has a projection 131 with a substantially semicircular cross section, and a contact portion 132 of a small area to be brought into contact with the inclined surface 113a of the tip piece 111 is formed of a summit portion of the projection 131.

A plurality of coupling members 122 (only one of which members is shown in FIGS. 17A and 17D) are provided in the sheath 11. As is shown in FIG. 17D, each coupling member 122 has a slit 123 which detachably receives the oscillation transmitting rod 43. Each coupling member 122 is made of a highly slidable fluorocarbon resin such as Teflon. The coupling members 122 are provided in those positions in the sheath 11 which correspond to the nodes of the ultrasonic oscillation generated from the ultrasonic transducer 51, so as not to be adversely affected by the ultrasonic oscillation.

The rear end of the sheath 11 is connected to the rotor 48 (FIG. 4) axially movably received in the hole 33b of the hand piece 2 and serving as connection means. The sheath 11 is pulled rearward via the rotor 48 when the movable handle 32 is moved toward the stationary handle 31. Thus, the pressing portion 118 of the sheath 11 is moved toward the treatment section 113 of the tip piece 111.

The treatment section 113 of the tip piece 111 is kept to project outward from the opening of the tip ring 114 of the sheath 11. As described above, the treatment section 113 of the tip piece 111 of the probe 52 and the contact portion 120a of the second elastic member 120 are inclined relative to the line perpendicular to the axis of the sheath 11. An organic tissue is disposed to be held between the inclined surface 113a of the treatment section 113 of the tip piece 111 and the second elastic member 120 of the pressing portion 118 of the reception member 117.

The operation of the ultrasonic incising/coagulating instrument according to the tenth embodiment will be described, taking, as an example, a case where the main body 1 of the ultrasonic incising/coagulating instrument is inserted in an abdominal cavity.

First, the tip of the main body 1 is moved to a target organic tissue. Subsequently, the movable handle 32 of the operating section 3 is moved toward the stationary handle 31, thereby clockwise rotating, about the handle support pin 34, the engagement claw 35a of the engagement member 35 of the movable handle 32 as shown in FIG. 15. Accordingly, the rotor 48 is pulled rearward by the engagement claw 35a along the axis of the sheath 11. As a result, the sheath 11 is moved rearward together with the rotor 48.

In accordance with the movement of the sheath 11 toward the proximal end of the instrument, the pressing portion 118 of the reception member 117 moves toward the treatment section 113 of the tip piece 111. As a result, the target organic tissue is held between the inclined surface 113a of the treatment section 113 of the tip piece 111 and the second elastic member 120 of the pressing portion 118 of the reception member 117.

In this state, an ultrasonic wave is generated by driving the ultrasonic transducer 51 in the hand piece 2. The ultrasonic wave generated by the ultrasonic transducer 51 is transmitted to the tip piece 111 via the horn 21 and the oscillation transmitting rod 43. The ultrasonic wave is then transmitted to the held organic tissue, thereby coagulating the same by frictional heat due to the ultrasonic wave.

While the ultrasonic oscillation is applied to the organic tissue, the movable handle 32 is further moved toward the stationary handle 31 to increase the force of holding of the tissue. Accordingly, the pressing portion 118 of the reception member 117 further approaches the treatment section 113 of the tip piece 111, with the result that the held organic tissue is excised without bleeding.

The probe 52 is supplied with a high frequency current, when necessary. When the tip piece 111 of the probe 52 is brought into contact with an organic tissue, with the high frequency current supplied thereto, it is used as an electric surgical knife and performs a high frequency treatment of the organic tissue.

The ultrasonic incising/coagulating instrument of the tenth embodiment constructed as above can provide the following advantages. The platelike treatment section 113 provided at the tip of the tip piece 111 has the inclined surface 113a as shown in FIG. 17A. Further, the pressing portion 118 of the hook-shaped reception member 117 projecting at the tip of the sheath 11 is inclined parallel to the inclined surface 113a of the tip piece 111. As a result, a contact portion between the treatment section 113 of the tip piece 111 of the probe 52 and the second elastic member 120 attached to the pressing portion 118 of the reception member 117 is inclined relative to the line perpendicular to the axis of the sheath 11.

Accordingly, when an organic tissue is held between the treatment section 113 of the tip piece 111 of the probe 52 and the second elastic member 120 at the pressing portion 118 of the reception member 117, ultrasonic oscillation is received by the surface of the pressing portion 118 of the sheath 11 which is inclined relative to the line perpendicular to the axis of the sheath 11. This means that part of the ultrasonic oscillation applied to the pressing portion 118 will escape therefrom, and hence that generation of a great amount of heat due to the oscillation will be avoided at the pressing portion 118. Thus, the hook-shaped reception member 117 of the sheath 11 is prevented from being damaged, and therefore the intensity of the ultrasonic wave at the time of an ultrasonic treatment is not limited, with the result that effective incising of an organic tissue can be performed using ultrasonic wave of a high output.

Moreover, as is shown in FIG. 18, the prism-shaped projection 121 shown in FIG. 19A is provided at that end of the second elastic member 120 of the pressing portion 118 which is opposed to the tip piece 111 of the probe 52, and the angle of the summit of the prism-shaped projection 121 is set substantially to 90° or more. Thus, the contact portion 120a of the projection 121 can be brought into line contact with the inclined surface 113a of the tip piece 111. This can effectively prevent generation of a great amount of heat at the pressing portion 118 of the sheath 11, thereby preventing damage of the hook-shaped reception member 117 of the sheath 11.

Although in the embodiment, the sheath 11 is formed of a fluorocarbon resin tube, it may be formed of a metal tube having its inner peripheral surface coated with a heat resistant and slippery material such as a fluorocarbon resin (e.g. Teflon).

Figure 20:
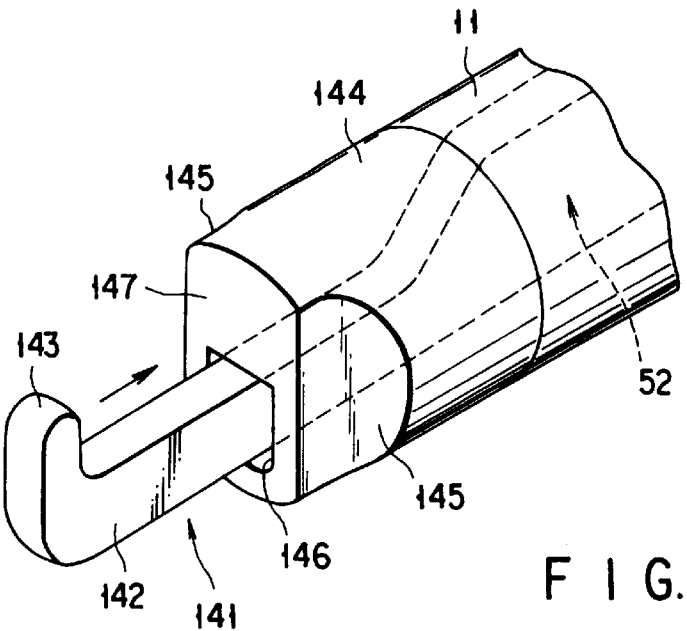
FIG. 20 is a perspective view, showing a front end treatment section of a probe and a front end pressing portion of a sheath in an eleventh embodiment.
Figure 21:
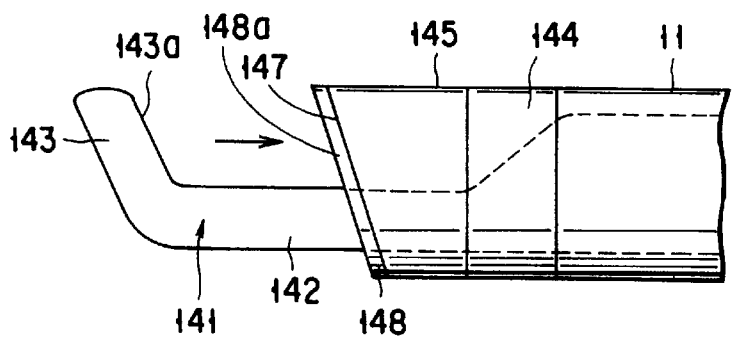
FIG. 21 is a side view, showing the front end treatment section of the probe and the front end pressing portion of the sheath in the eleventh embodiment.

Referring then to FIGS. 20 and 21, an ultrasonic incising/coagulating instrument according to an eleventh embodiment will be described. This embodiment differs from the tenth embodiment (shown in FIGS. 15–19A) in that the former employs a reception member as described below in place of the reception member 117 employed in the latter.

In this embodiment, a hook-shaped treatment section 141 of a substantially L shape is provided at the tip of the probe 52 in place of the tip piece 111 employed in the tenth embodiment. The hook-shaped treatment section 141 has an axial member 142 and a substantially L-shaped hook 143.

Further, the sheath 11 has a substantially cylindrical reception member 144 at its front end. The reception member 144 has a tapered restriction portion 145 at its front end. The hook 143 of the hook-shaped treatment section 141 projects outward through an opening 146 formed in the front end face of the restriction portion 145. The remaining portion of the front end face, which is opposed to the hook 143 of the hook-shaped treatment section 141, constitutes a pressing face 147.

In this embodiment, at the time of operating the movable handle 32, the sheath 11 is kept immovable, and the tip treatment section 141 of the probe 52 is moved toward the reception member 144 of the sheath 11, thereby moving the sheath 11 and the probe 52 relative to each other.

As shown in FIG. 21, the hook 143 of the hook-shaped treatment section 141 of the probe 52 has an inclined surface 143a corresponding to the pressing portion 118 employed in the tenth embodiment (FIGS. 15–19A). In addition, the pressing face 147 of the reception member 144 has a second elastic member 148 as in the tenth embodiment. The second elastic member 148 has an inclined portion 148a parallel to the inclined surface 143a of the hook 143 of the hook-shaped treatment section 141.

Thus, a contact portion 148a between the hook 143 of the hook-shaped treatment section 141 of the probe 52 and the second elastic member 148 of the reception member 144 is inclined relative to the line perpendicular to the axis of the sheath 11, as in the tenth embodiment. Accordingly, also in the eleventh embodiment, part of ultrasonic oscillation applied to the pressing face 147 of the reception member 144 of the sheath 11 will escape therefrom, and hence generation of a great amount of heat due to the oscillation will be avoided at the pressing face 147.

Figure 22:
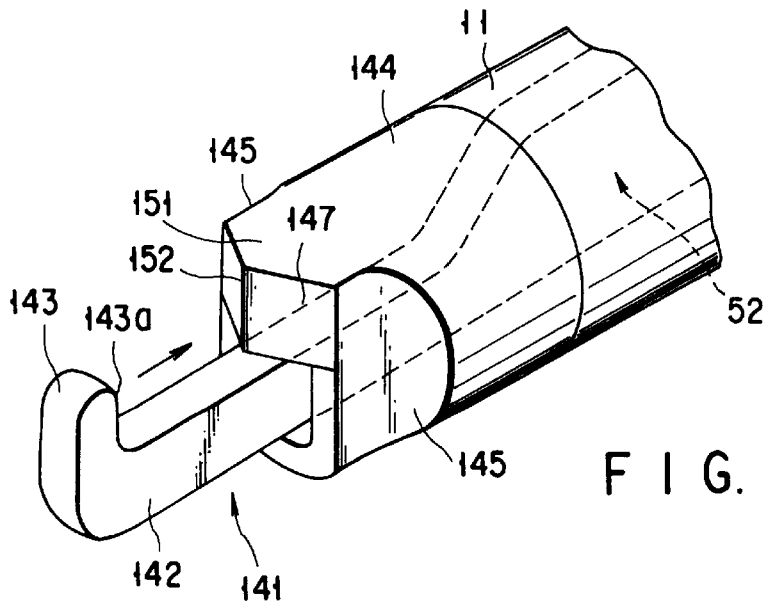
FIG. 22 is a perspective view, showing a front end treatment section of a probe and a front end pressing portion of a sheath in a twelfth embodiment.

FIG. 22 shows a twelfth embodiment of the invention. This embodiment is obtained by modifying the reception member 144 of the eleventh embodiment as follows:

Specifically, in the twelfth embodiment, a tapered projection 151 is provided on the pressing face 147 of the reception member 144. The projection 151 has a tip edge portion 152 to be brought into line contact with the inclined face 143a of the hook 143.

By virtue of this structure, part of ultrasonic oscillation applied to the pressing face 147 of the reception member 144 of the sheath 11 can escape therefrom, and hence generation of a great amount of heat due to the oscillation can be avoided at the pressing face 147, as in the eleventh embodiment.

The edge portion 152 of the projection 151 employed in this embodiment, which is put into line contact with the inclined face 143a of the hook 143, can more effectively prevent generation of a great amount of heat at the pressing face 147 than in the eleventh embodiment.

It is a matter of course that the invention is not limited to the above-described embodiments, but may be modified in various manners without departing the scope thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. An ultrasonic treatment instrument comprising:
   an ultrasonic transducer for generating ultrasonic oscillation;
   a hand piece containing the ultrasonic transducer;
   a probe having a proximal end portion connected to the ultrasonic transducer and a distal end portion to which the ultrasonic oscillation of the ultrasonic transducer is transmitted;
   a sheath covering the probe and having a front end portion extending toward the distal end portion of the probe and a rear end portion connected to the hand piece;
   a hook-shaped treatment section provided at the distal end portion of the probe and having a hook portion bent substantially perpendicular to an axis of the sheath and an axial body extending from a proximal end of the bent hook portion, said axial body being eccentric with respect to the axis of the sheath; and
   an operating section which moves the sheath and the probe relative to each other along the axis of the sheath to thereby enable an organic tissue to be held between the hook-shaped treatment section and the front end portion of the sheath.

2. The instrument according to claim 1, further comprising a second sheath provided around the first-mentioned sheath and movable relative to the first-mentioned sheath along the axis of the first-mentioned sheath.

3. The instrument according to claim 1, wherein at least one of an inner peripheral surface of the sheath and an outer peripheral surface of the probe, which are brought into contact with each other, comprises a compliant material.

4. The instrument according to claim 1, wherein the sheath comprises a polytetrafluoroethylene tube.

5. The instrument according to claim 1, wherein the hook-shaped treatment section is integrally coupled to the distal end portion of the probe.

6. The instrument according to claim 1, wherein the hook-shaped treatment section includes a wire member having a proximal end portion thereof fixed to the distal end portion of the probe, said wire member being bent, at a tip portion thereof, to form the hook portion which is bent substantially perpendicular to the axis of the sheath.

7. The instrument according to claim 6, wherein at least a part of the hook-shaped treatment section, which is fixed to the distal end portion of the probe, is situated coaxially with respect to the probe.

8. The instrument according to claim 1, wherein the probe comprises a linear slot provided at a distal end portion thereof, and wherein the hook portion of the hook-shaped treatment section comprises a substantially L-shaped plate member having a proximal end portion which is securely fitted in the linear slot provided at the distal end portion of the probe.

9. The instrument according to claim 1, wherein the hand piece comprises rotary operating means for rotating the sheath and the hook-shaped treatment section about an axis of the probe, together with the probe.

10. An ultrasonic treatment instrument comprising:

an ultrasonic transducer for generating ultrasonic oscillation;

a hand piece containing the ultrasonic transducer;

a probe having a proximal end portion connected to the ultrasonic transducer and a distal end portion to which the ultrasonic oscillation of the ultrasonic transducer is transmitted;

a sheath covering the probe and having a front end portion extending toward the distal end portion of the probe and a rear end portion connected to the hand piece;

a hook-shaped treatment section provided at the distal end portion of the probe and having a hook portion bent substantially perpendicular to an axis of the sheath; and an operating section which moves the sheath and the probe relative to each other along the axis of the sheath to thereby enable an organic tissue to be held between the hook-shaped treatment section and the front end portion of the sheath;

wherein the sheath has, at the front end portion thereof, a reception member for receiving the organic tissue pressed thereto by the hook portion of the hook-shaped treatment section; and wherein the reception member has a front open end with a substantially elliptic shape corresponding to a shape of a front end portion of the hook portion of the hook-shaped treatment section.

11. The instrument according to claim 10, wherein the reception member has a pressing face corresponding to an opposed portion of the hook portion and partially closing the front open end of the reception member.

12. The instrument according to claim 11, wherein a part of the hook portion of the hook-shaped treatment section which is brought into contact with the organic tissue has a first inclined surface, and wherein the pressing face comprises a second inclined surface corresponding to the first inclined surface.

13. The instrument according to claim 12, wherein the first inclined surface of the hook portion is inclined such that a distal end portion of the first inclined surface is more remote from the sheath than a proximal end portion of the first inclined surface.

14. The instrument according to claim 12, wherein the second inclined surface comprises a line contact portion to be brought into line contact with the first inclined surface.

15. The instrument according to claim 10, wherein the reception member has, at a proximal end thereof, a coupling portion coupled with the sheath and having an inner diameter smaller than an inner diameter of the front end portion of the sheath.

16. The instrument according to claim 10, wherein the reception member comprises polytetrafluoroethylene.

17. The instrument according to claim 10, wherein the reception member comprises a space having a width set in accordance with a coagulating force of the instrument, said space being formed between a peripheral surface defining the front open end of the reception member and a side surface of the hook portion of the hook-shaped treatment section.

18. The instrument according to claim 10, wherein a front portion of the reception member comprises a tapered restriction portion.

19. The instrument according to claim 10, wherein the hook portion of the hook-shaped treatment section comprises a treatment end face opposed to the reception member, and slip preventing means for preventing the organic tissue held between the treatment end face and the reception member from escaping therefrom, said slip preventing means comprising means for rendering a distance between the treatment end face and the reception member more narrow on a distal end side of the hook portion than on a proximal end side of the hook portion.

20. The instrument according to claim 19, wherein the slip preventing means comprises means for setting the treatment end face perpendicular to an axis of the probe, and wherein the reception member comprises an inclined front end face inclined relative to the axis of the probe.

21. The instrument according to claim 19, wherein the slip preventing means comprises means for setting a front end face of the reception member perpendicular to an axis of the probe, and wherein the treatment end face is inclined relative to the axis of the probe.

22. The instrument according to claim 19, wherein the slip preventing means comprises means for setting a front end face of the reception member inclined relative to an axis of the probe, and wherein the treatment end face is inclined relative to the axis of the probe in a direction opposite to a direction in which the front end face of the reception member is inclined.

* * * * *